(12) United States Patent
Korman

(10) Patent No.: US 12,186,001 B2
(45) Date of Patent: Jan. 7, 2025

(54) TARGETING GUIDE

(71) Applicant: WRIGHT MEDICAL TECHNOLOGY, INC., Memphis, TN (US)

(72) Inventor: Zachary Korman, Memphis, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 442 days.

(21) Appl. No.: 17/663,691

(22) Filed: May 17, 2022

(65) Prior Publication Data

US 2022/0401140 A1 Dec. 22, 2022

Related U.S. Application Data

(60) Provisional application No. 63/211,597, filed on Jun. 17, 2021, provisional application No. 63/247,899, filed on Sep. 24, 2021.

(51) Int. Cl.
*A61B 17/88* (2006.01)
*A61B 17/56* (2006.01)

(52) U.S. Cl.
CPC ...... *A61B 17/8872* (2013.01); *A61B 17/8866* (2013.01); *A61B 17/8875* (2013.01); *A61B 2017/565* (2013.01)

(58) Field of Classification Search
CPC ............ A61B 17/8872; A61B 17/8866; A61B 17/8875; A61B 2017/565
See application file for complete search history.

(56) References Cited

U.S. PATENT DOCUMENTS 8,343,199 B2  1/2013  Tyber et al.
2007/0233112 A1  10/2007  Orbay et al.
(Continued)

FOREIGN PATENT DOCUMENTS

FR    3051349 A1    11/2017
WO  2020041841 A1    3/2020

OTHER PUBLICATIONS

Extended European Search Report issued in connection with corresponding European Patent Application No. 22174220.8, Nov. 11, 2022, 9 pages.
(Continued)

*Primary Examiner* — Tracy L Kamikawa
(74) *Attorney, Agent, or Firm* — DUANE MORRIS LLP

(57) ABSTRACT

An assembly includes a first portion including an anchor pivotally attached to a first end of the first portion, the anchor to be inserted into an intramedullary canal of a first bone fragment; a second portion pivotally attached to a second end of the first portion and including a first skin-interfacing portion; a second skin-interfacing portion to interface with and secure the assembly to skin adjacent to the first bone fragment; and an actuation mechanism attached between the first portion and the second portion that actuates pivoting of the second portion to the first portion; wherein a lateral force is generated between the first skin-interfacing portion against a second bone fragment, adjacent to the first bone fragment, and a holding force is provided by the anchor when the actuation mechanism is actuated, so the first portion pivots with respect to second portion, while the anchor is in the intramedullary canal.

14 Claims, 15 Drawing Sheets

(56) References Cited

U.S. PATENT DOCUMENTS

| | | |
|---|---|---|
| 2009/0036931 A1 | 2/2009 | Pech et al. |
| 2014/0088594 A1 | 3/2014 | Sasing |
| 2014/0180348 A1 | 6/2014 | Thoren et al. |
| 2015/0305791 A1 | 10/2015 | Purohit |
| 2015/0359580 A1 | 12/2015 | Dacosta et al. |
| 2017/0196602 A1 | 7/2017 | Lunquist et al. |
| 2018/0242987 A1 | 8/2018 | Lintula et al. |
| 2018/0242988 A1 | 8/2018 | Dacosta et al. |
| 2021/0113223 A1 | 4/2021 | Schaumann et al. |
| 2021/0330311 A1* | 10/2021 | Denham ............... A61B 17/025 |
| 2022/0039810 A1* | 2/2022 | Gil ..................... A61B 17/1775 |
| 2022/0192685 A1* | 6/2022 | Gazonnet ........... A61B 17/1739 |

OTHER PUBLICATIONS

International Search Report and Written Opinion issued in connection with International Patent Application No. PCT/US2021/018293, Jun. 29, 2021, 18 pages.

* cited by examiner

TARGETING GUIDE

CROSS REFERENCE TO RELATED APPLICATIONS

This application claims the benefit of United States Provisional Application No. 63/211,597, filed Jun. 17, 2021, and United States Provisional Application No. 63/247,899, filed Sep. 24, 2021, which are incorporated by reference for all purposes as if fully set forth herein.

FIELD OF DISCLOSURE

The disclosed system and method relate to the field of correcting anatomical structures. The disclosure relates to a bone alignment and screw drill targeting guide to use in surgical procedures to correct hallux valgus deformity (i.e., bunions). More particularly, the disclosure is directed to an assembly that shifts, stabilizes, and targets osteotomy fragments during minimally invasive osteotomy surgery.

BACKGROUND OF THE INVENTION

Hallux valgus deformities occur when a metatarsal goes into a varus state (i.e., is pointed inwardly). In addition to being pointed inward, the metatarsal also may be rotated about its longitudinal axis such that the bottom of the bone is facing outwardly, which may result in the sesamoid being pointed outwardly when it should be located underneath the metatarsal. Correction of a bunion typically requires surgery and many techniques have been developed to correct hallux valgus deformities based on the deformity and the condition of the patient.

During a minimally invasive Chevron and Akin osteotomy (MICA) procedure for correcting hallux valgus deformity, a Chevron osteotomy is made in the first metatarsal bone separating the head portion, the capital fragment, of the first metatarsal from the remainder of the metatarsal, the proximal fragment. The metatarsal head is then shifted laterally and fixed with two screws. K-wires are traditionally used to hold the metatarsal head at the intended translated position during the subsequent screw fixation procedure. Achieving the desired K-wire trajectory can be difficult. Therefore, a guiding instrument for setting the trajectory of the K-wire is desired.

Current technology does not allow easy lateral translation of the capital fragment after a distal first metatarsal osteotomy (made in the correction of Hallux Valgus) in such a way that the translation is controlled and maintained without requiring the user to rely on hand tools to hold the bones in place. This situation eliminates a user from being used for other tasks. Additionally, force applied by hand tools can cause the bones to shift relative to each other. Furthermore, current technology also does not allow reproducible and easy targeting of the capital fragment such that screws can follow an appropriate trajectory per state-of-the-art surgical techniques.

SUMMARY OF THE INVENTION

To overcome the problems described above, embodiments of the invention provide a mechanism and method that controls lateralization of the capital fragment. This is accomplished via an intramedullary hook in the proximal fragment, a skin-interfacing wedge located against the capital fragment, and a screw mechanism to change the relative position of these two components. Furthermore, embodiments include a targeting mechanism that aims at a target location in a certain proximity to the capital-fragment-engaging wedge such that wire sleeves can facilitate the placement of a guide pin down an idealized trajectory.

Accordingly, various embodiments of the invention ease lateral translation of the capital fragment after a distal first metatarsal osteotomy in such a way that the translation is controlled.

According to one embodiment, an assembly includes a first portion including an anchor pivotally attached to a first end of the first portion, the anchor configured to be inserted into an intramedullary canal of a first bone fragment; a second portion pivotally attached to a second end of the first portion and including a first skin-interfacing portion; a second skin-interfacing portion to interface with and secure the assembly to skin of a patient's foot; and an actuation mechanism attached between the first portion and the second portion that actuates a pivoting of the second portion with respect to the first portion; wherein a first lateral force is generated between the first skin-interfacing portion against a second bone fragment, adjacent to the first bone fragment, and a holding force is provided by the anchor when the actuation mechanism is actuated, so that the first portion pivots with respect to second portion, while the anchor is located in the intramedullary canal.

One assembly can further include a trajectory cartridge attached to the first portion or the second portion and including a first channel aligned to project a trajectory line to the second bone fragment. The trajectory cartridge can include a plurality of channels including the first channel that are aligned to each project a trajectory line to the second bone fragment. A longitudinal axis along a length of the first channel of the plurality of channels can be parallel to a longitudinal axis along a length of a second channel of the plurality of channels. The first channel can be configured to receive a targeting sleeve and the second channel can be configured to receive a guide wire.

In some embodiments, the second portion can be pivotally attached to the first portion via a sliding pin within a curved slot. The second skin-interfacing portion can include a guide attached to the second portion. The first skin-interfacing portion can be wedge shaped.

A surgical instrument kit is also provided that may include an assembly according to the invention with a trajectory cartridge attachable to the assembly and including a first channel aligned to project a first trajectory line to the second bone fragment. The kit may include a guide to attach the assembly and the targeting cartridge. The kit may also include a plurality of trajectory cartridges, wherein each of the plurality of trajectory cartridges includes a different configuration of a channel aligned to project a trajectory line to the second bone fragment.

The kit may further include a plurality of targeting sleeves and a plurality of fixation wires, with a tissue protector sleeve, in some embodiments, configured to receive a screw to be inserted into a first bone fragment and a second bone fragment.

The kit may additionally include a corner removal guide to guide removal of a portion of a first bone fragment wherein the corner removal guide includes a plurality of guide holes, a first of which is configured to receive a screwdriver for a screw fixed to the first and second bone fragments, and a second which is configured to guide the removal of the portion of the first bone fragment.

A method for correcting a hallux valgus deformities is provided that includes bisecting a metatarsal; inserting an anchor that is attached to a first portion of an actuation mechanism into an intramedullary canal of a proximal fragment of the metatarsal; and actuating the actuating mechanism to generate a lateral force between a position of the anchor and a first skin-interfacing portion at a second portion of the actuation mechanism located against a capital fragment of the metatarsal or medial skin of the capital fragment of the metatarsal.

The method may also include inserting a guide wire through the trajectory cartridge; and aligning a longitudinal axis of the guide wire to a longitudinal axis of a fixation wire sleeve.

The method may further include attaching a trajectory cartridge to the second portion; and inserting a fixation wire through the trajectory cartridge, the proximal fragment, and into a target location of the capital fragment to fix the location of the capital fragment relative to the proximal fragment. The method may also include inserting a screw down the fixation wire, through the proximal fragment, and into the capital fragment.

The method may additionally include detaching the trajectory cartridge from the anchor guide; inserting a skin protection sleeve over the fixation wire; and inserting a screw down the fixation wire, through the skin protection sleeve, through the proximal fragment, and into the capital fragment.

The method may also provide for extracting the anchor from the metatarsal; inserting a corner removal guide over the fixation wire or a screwdriver that is used to insert the screw; and removing a portion of the proximal bone fragment based on a guide hole in the corner removal guide.

BRIEF DESCRIPTION OF THE DRAWINGS

These and other features and advantages of the apparatuses and methods described herein will be more fully disclosed in, or rendered obvious by, the following detailed description of the preferred embodiments, which is to be considered together with the accompanying drawings wherein like numbers refer to like parts.

DETAILED DESCRIPTION

Figure 1:
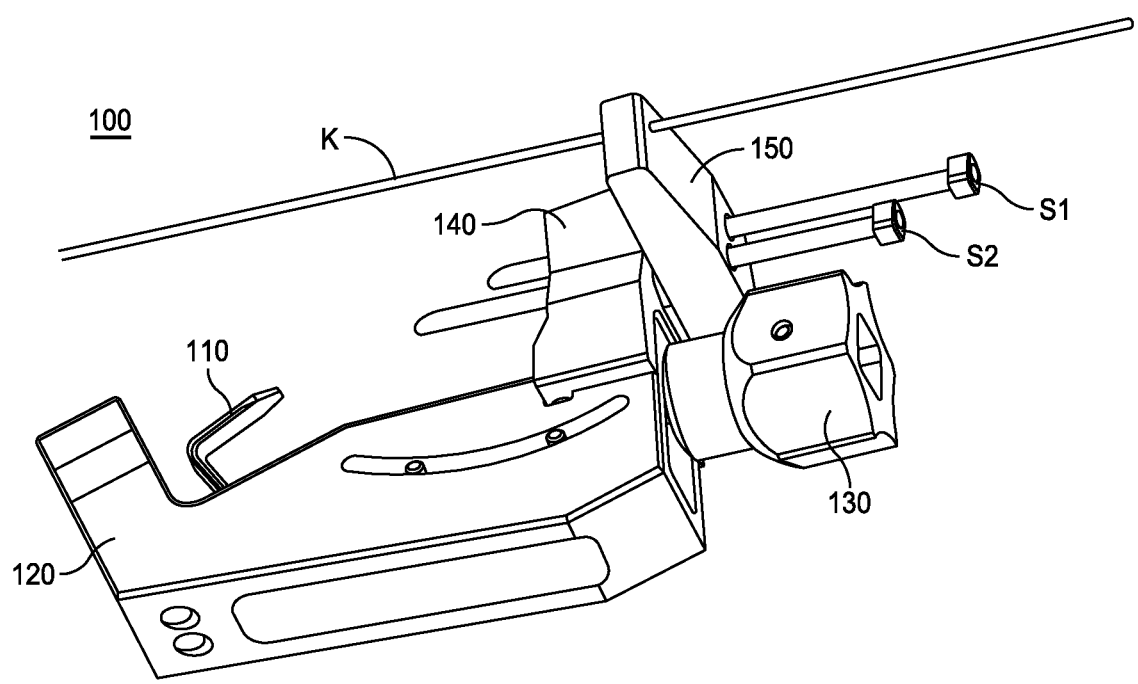
FIGS. 1 and 2 are perspective views of an assembled trajectory cartridge according to an embodiment of the invention.

This description of the exemplary embodiments is intended to be read in connection with the accompanying drawings, which are to be considered part of the entire written description. The drawing figures are not necessarily to scale and certain features of the invention may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Figure 2:
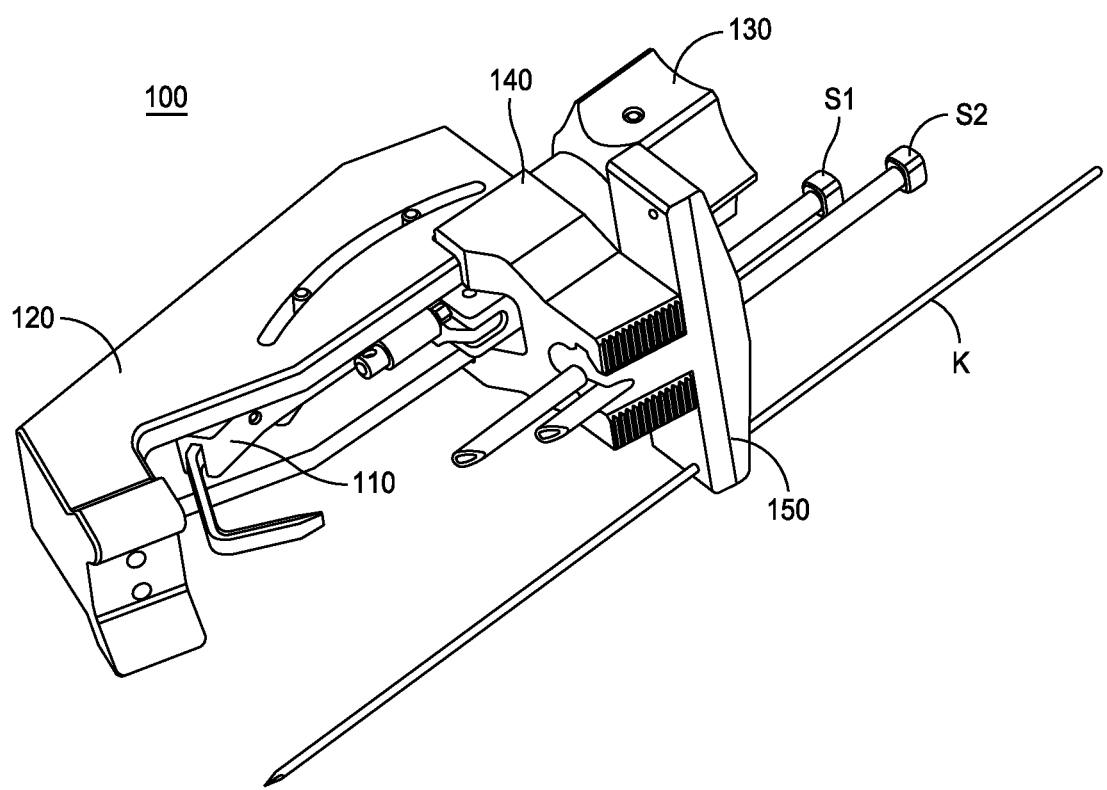
Figure 3:
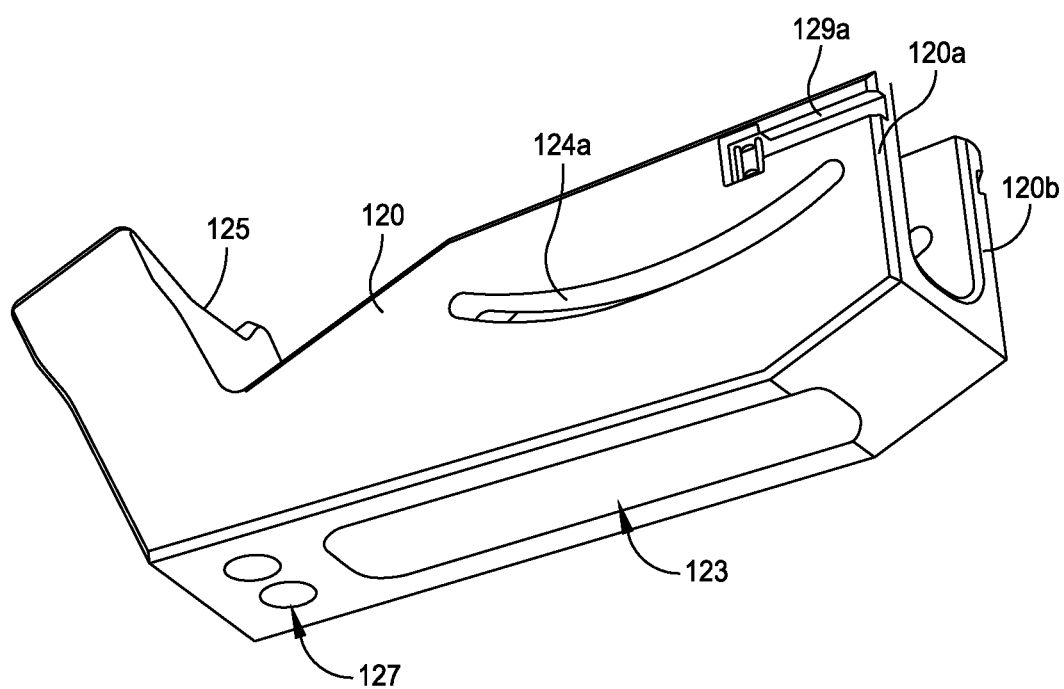
FIGS. 3 and 4 are perspective views of an outer portion of the assembly.
Figure 4:
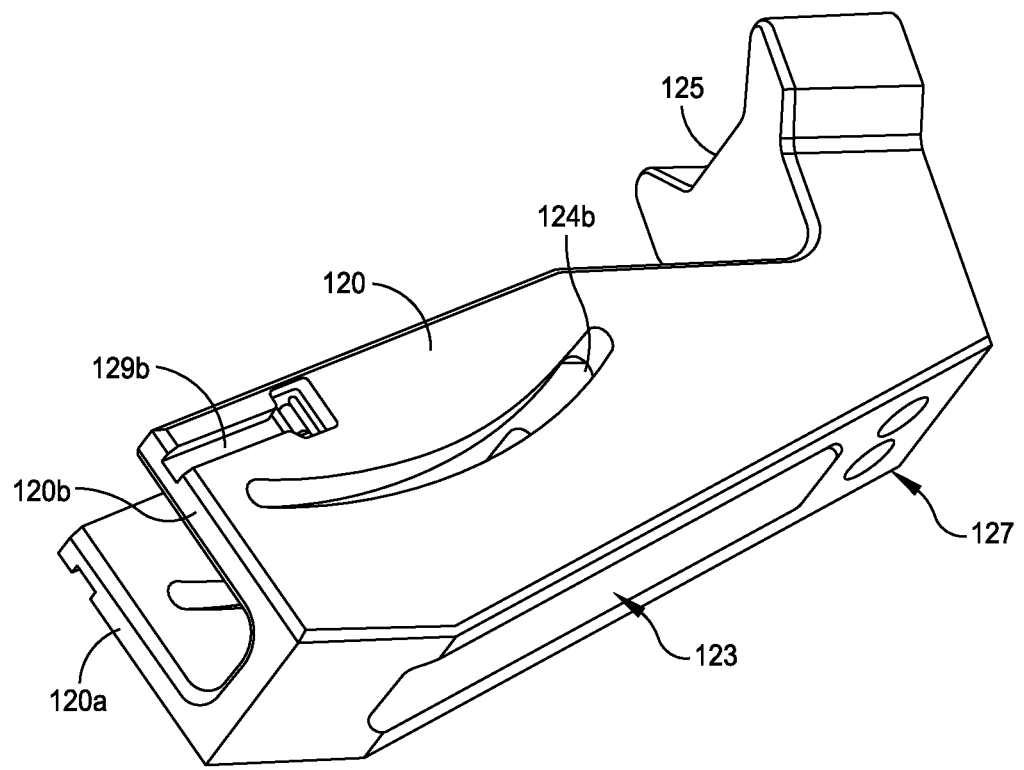

Referring to FIGS. 1 and 2, an assembly 100 may be used to facilitate a distal metatarsal osteotomy for bunion correction via a minimally invasive surgical (MIS) procedure. FIGS. 1 and 2 show that the system 100 can include an inner portion 110; an outer portion 120; an actuation mechanism 130; a guide 140; a trajectory cartridge 150; sleeves S1 and S2; and a K-wire K. Referring to FIGS. 3 and 4, the outer portion 120 can include a substantially U-shaped body with a first side 120a and an opposing second side 120b. Each of the first side 120a and the second side 120b can respectively include a curved slot 124a and 124b to receive guide pins from the inner portion 110. The outer portion 120 can also include an opening 123 in the body and a skin-interfacing portion 125 at one end of the body. As shown, the skin-interfacing portion 125 can be substantially V-shaped, U-shaped, or wedge shaped. Optionally, guide holes 127 can be included through the body and the skin-interfacing portion 125 to guide a fixation element into an adjacent bone fragment. Additionally, each of the first side 120a and the second side 120b can respectively include a recess 129a, 129b used as mounting features to mount the guide 140 in the assembly 100.

Figure 5:
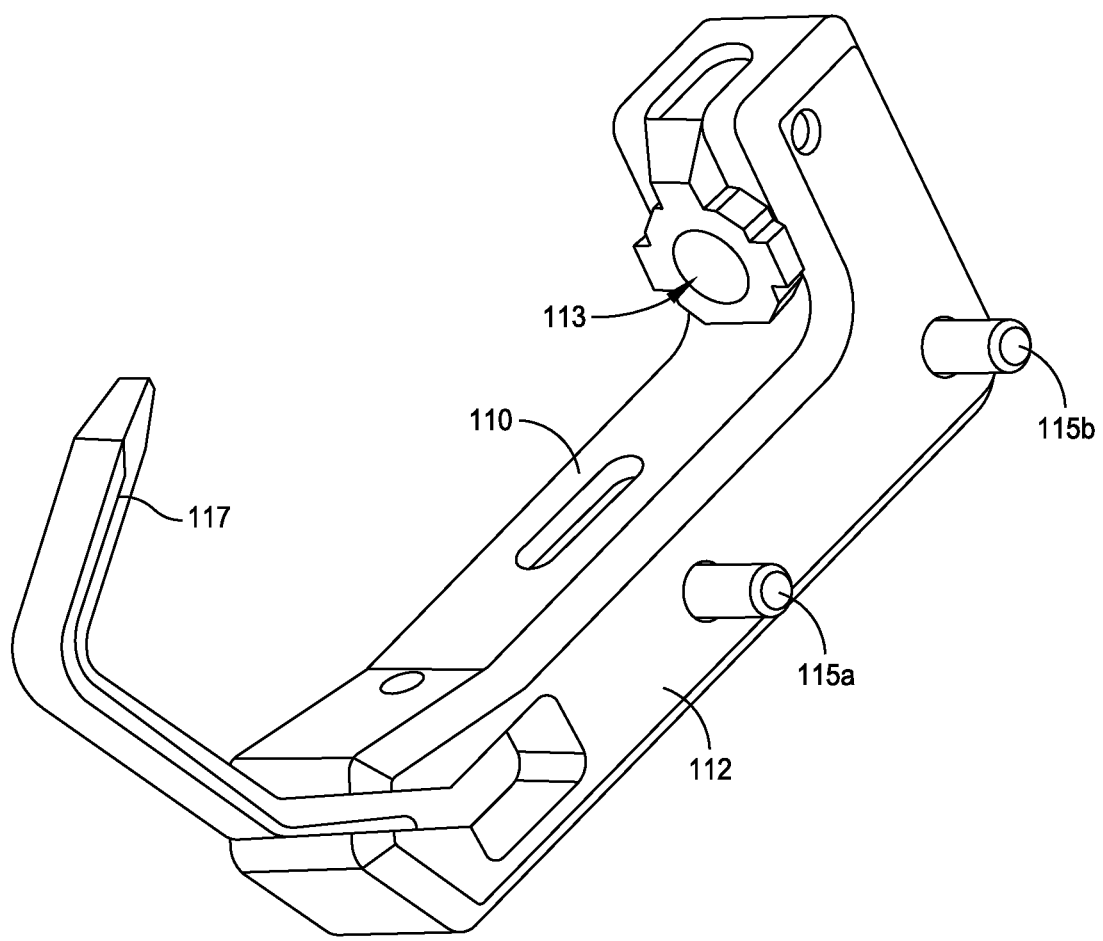
FIGS. 5-7 are perspective views of an inner portion of the assembly.
Figure 6:
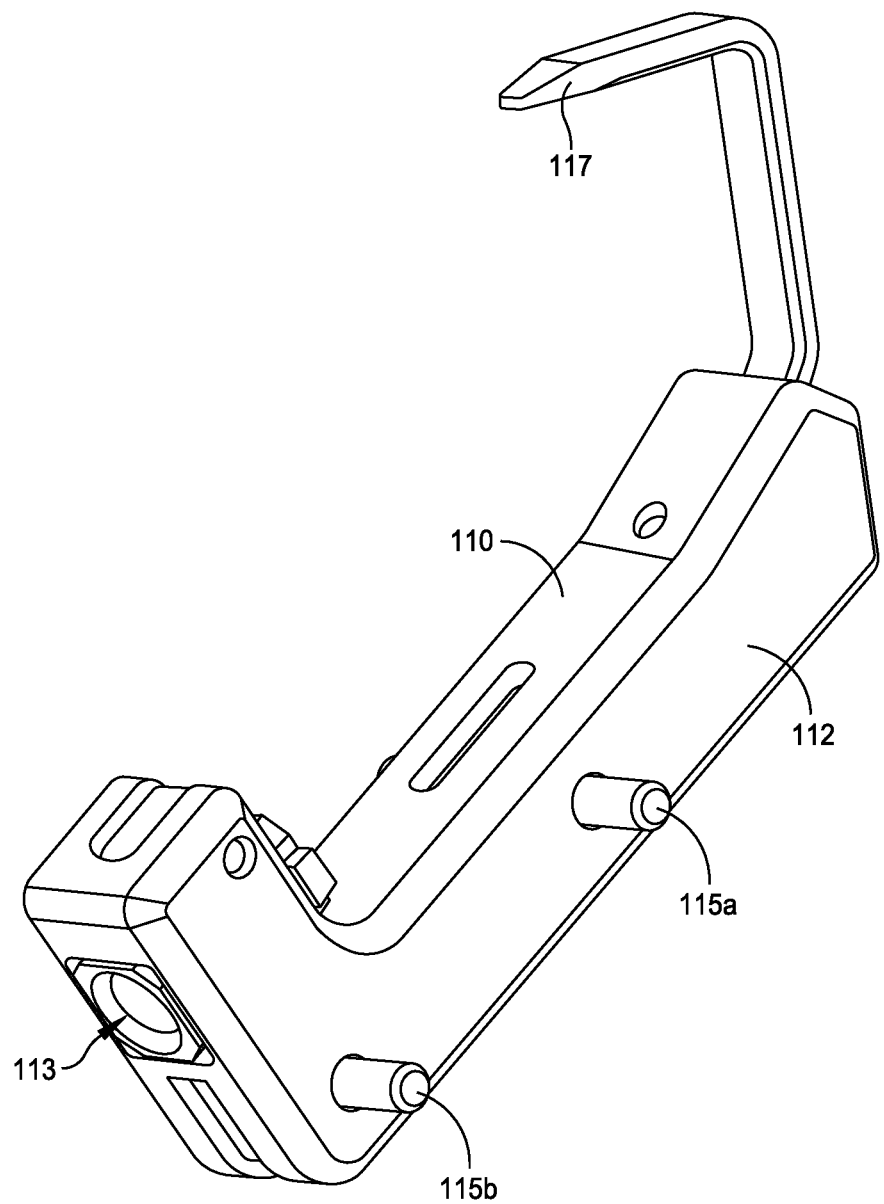
Figure 7:
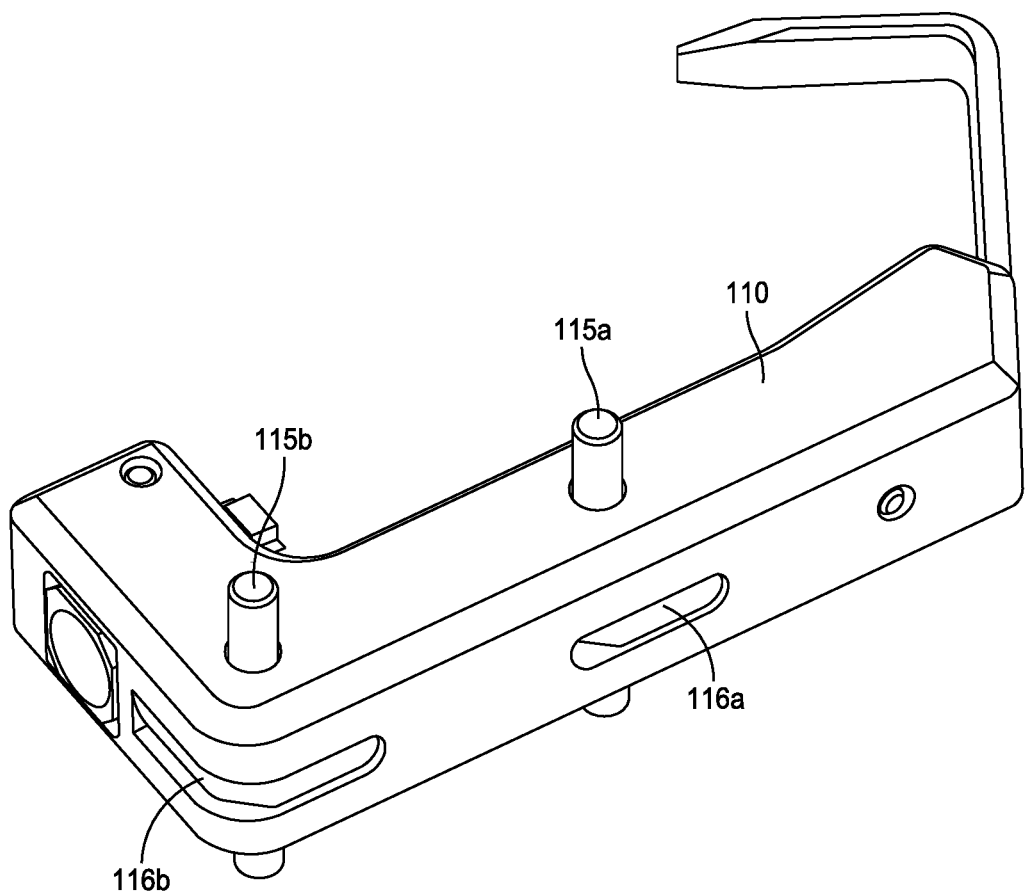

Referring to FIGS. 5-7, the inner portion 110. The inner portion 110 can include a substantially L-shaped body 112 that has a bore 113 through one end. The bore 113 can be threaded and configured to receive a mating threaded stem of the actuation mechanism 130. Additionally, the inner portion 110 can include guide pins 115a and 115b that protrude out from the body 112 and are configured to fit into the curved slots 124a and 124b of the outer portion 120. The cooperation of the guide pins 115a and 115b and the curved slots 124a and 124b provide a pivotal engagement between the inner portion 110 and the outer portion 120 further discussed below. The guide pins 115a and 115b can be dowel pins pressed through the body 112. Additionally, the inner portion 110 can include a curved hook-like structure as an anchor that includes a tip 117.

Still referring to FIG. 7, the inner portion 110 can include inserts 116a and 116b fit into cavities defined in the body 112. The inserts 116a and 116b can be configured to receive the dowel pins 115a and 115b that are press fit through the respective insert 116a, 116b to secure the dowel pins 115a, 115b to the inner portion. The inserts 116a, 116b can be made of a stronger material with tighter manufacturing tolerances to provide a firmer and more robust frictional press fit of the dowel pins 115a, 115b. Optionally, the inserts 116a, 116b can be omitted and the dowel pins 115a, 115b can be pressed into holes in the body 112 of the inner portion 110. Additionally, the anchor includes a hook-like structure with the tip 117 can be fit into a cavity defined in the body 112 and secured into place with a dowel pin or another type of fastener. Additionally, the bore 113 can be included in a separate component that can be fit into a cavity defined in the body 112 and secured into place with a dowel pin or other type of fastener.

Figure 8:
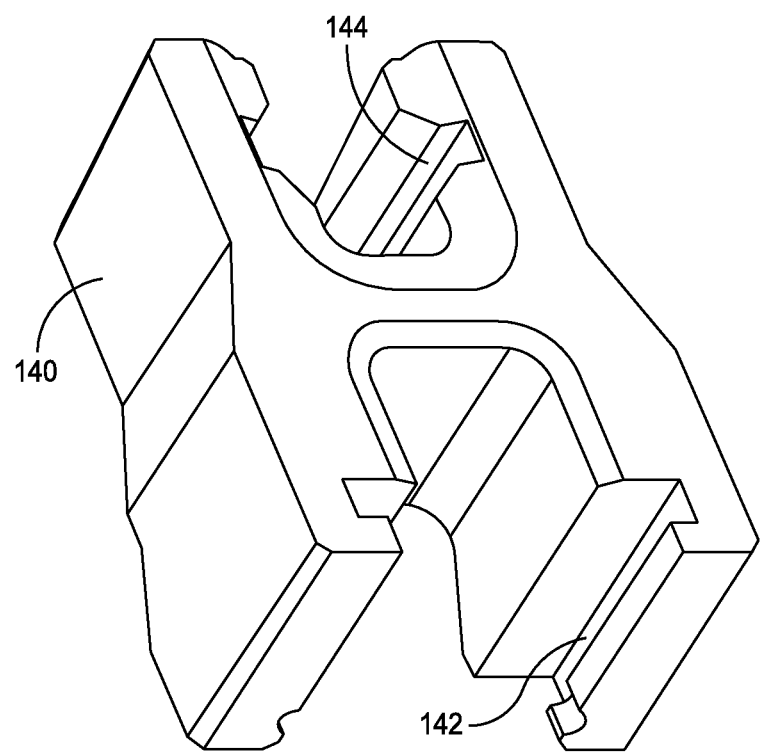
FIG. 8 is a perspective view of a guide used in any of the foregoing assemblies.

Referring to FIG. 8, shows the guide 140 can be substantially H-shaped and include attachment features to attach the guide 140 to the outer portion 120 and the trajectory cartridge 150. As shown, the guide 140 can include an attachment feature 142 with protrusions and grooves that are configured to fit into and securely mate with the recesses 129a, 129b of the outer portion 120. Additionally, the guide 140 can include an attachment feature 144 with protrusions and grooves that are configured to mate with corresponding features on the trajectory cartridge 150 as shown in FIGS. 2 and 9.

Figure 9:
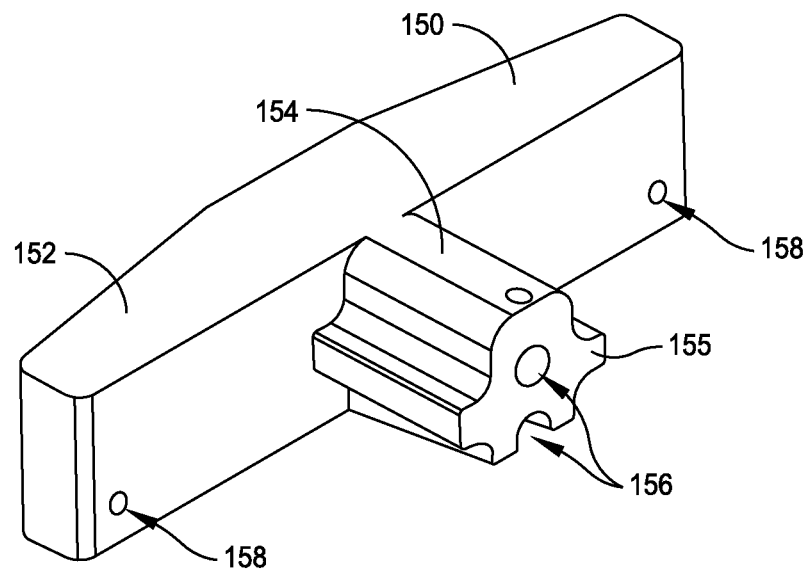
FIGS. 9 and 10 are perspective views of a trajectory cartridge for use in any of the foregoing assemblies.
Figure 10:
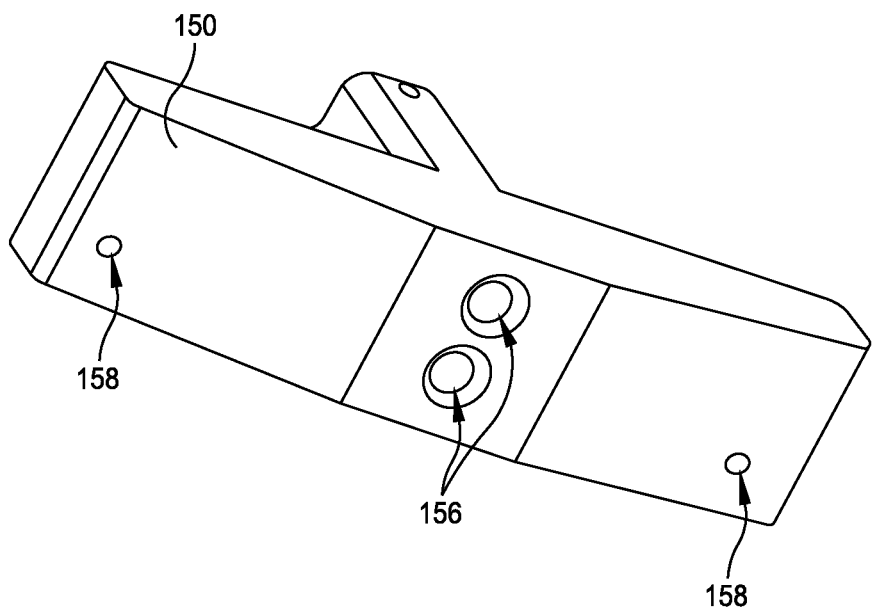

Referring to FIGS. 9 and 10, the trajectory cartridge 150 may be substantially T-shaped and include an elongated body 152 with a protruding portion 154 protruding from a central portion of the body 152. The protruding portion 154 can include protrusions 155 and/or groves that are configured to be pressed in and securely mate with corresponding features on the guide 140. Additionally, the trajectory cartridge 150 can include guide or sleeve holes 156 that extend through the body 152 and the protruding portion 154. The sleeve holes 156 can each be configured to receive a sleeve S1/S2 used as trajectory guides for fastening or guide elements. The guide or sleeve holes 156 can be substantially parallel to a right angle defining a longitudinal axis in which the protruding portion 154 protrudes from the body 152 or can be at a small angle to the longitudinal axis in which the protruding portion 154 protrudes to facilitate a slightly shifted target location at the metatarsal head. Additionally, the trajectory cartridge 150 can include indicator holes 158 configured to receive K-wires K.

The outer portion 120, the body 112 of the inner portion 110, the guide 140, and the trajectory cartridge 150 can all be made of plastic and can be press fit, slid, or snapped together. Optionally, these components may be made from plastic, metal, metal alloy, composite, ceramic, or any other suitable material or combinations thereof. Any or all of the portions of these components can be made via casting, molding, machining, injection molding, 3D printing, any other suitable manufacturing process, or combinations thereof.

The actuation mechanism 130 may include a knob or handle at a first end configured so that a user can rotate it and a threaded stem at a second end that mates through and is secured to the bore 113 of the inner portion 110. The actuation mechanism 130 is inserted through the opening 123 in the outer portion 120 and includes a threaded stem that threadedly engages the he bore 113 of the inner portion 110. The actuation mechanism 130 is wider than the opening 123 between the two sides 120a, 120b of the outer portion 120 so that by turning the knob, the threaded engagement between the actuation mechanism 130 and the inner portion 110 moves the relative orientation of the inner portion 110 with respect to the outer portion 120. Thus, the actuation mechanism 130 can be used to orient and align the assembly 100.

Figure 11:
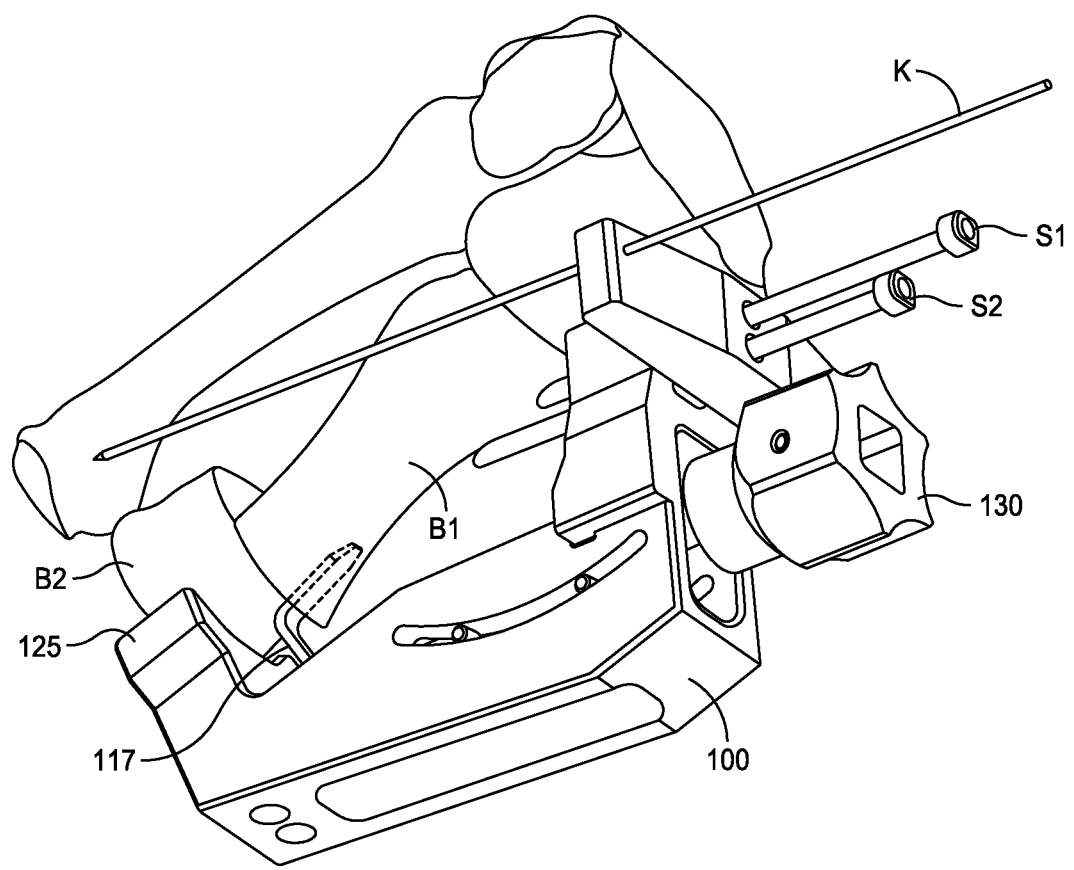
FIG. 11 is a perspective view of one of the foregoing assemblies in position adjacent to a first metatarsal bone.
Figure 13:
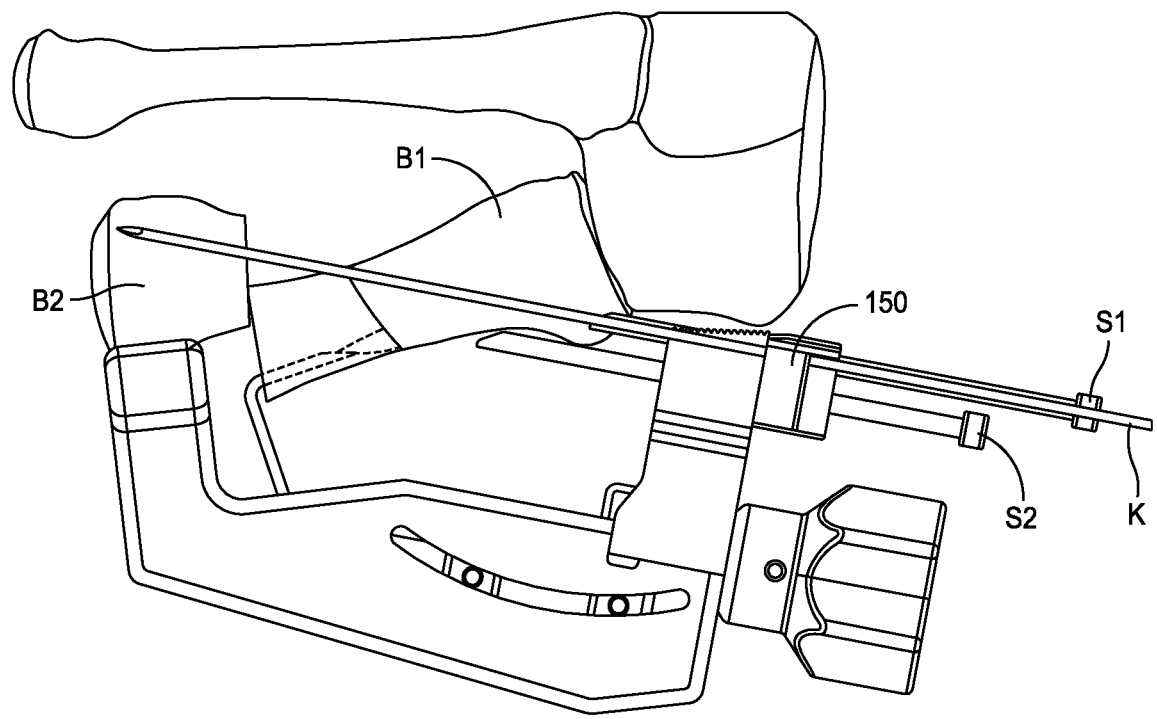
FIG. 13 is a perspective view, similar to that of FIG. 11, illustrating an alignment of a K-wire and a sleeve using the assembly.

Referring to FIG. 11, assembly 100 orients sleeves S1 and S2 to target and facilitates the placement of a guide pin(s) down an idealized trajectory through two portions of a bone after a first metatarsal bone has been cut into a first bone portion B1 (proximal fragment) and a second bone portion B2 (capital fragment). Although some figures include skeletal images of a patient's foot, it should be understood that the skin-interfacing portion 125 and the guide 140 are meant to contact the outside surface of the patient's skin, which is not depicted in the drawings. Referring to FIGS. 11 and 13, the guide 140 can be placed adjacent to the patient's foot, which could be at the first bone fragment; and/or proximal to the first bone fragment, typically at the cuneiform bone; and/or proximal to the cuneiform bone, depending on the size of the patient's foot. The tips of the targeting sleeves S1, S2 are meant to be inserted into a small incision such that they contact the patient's first bone portion B1.

Figure 12:
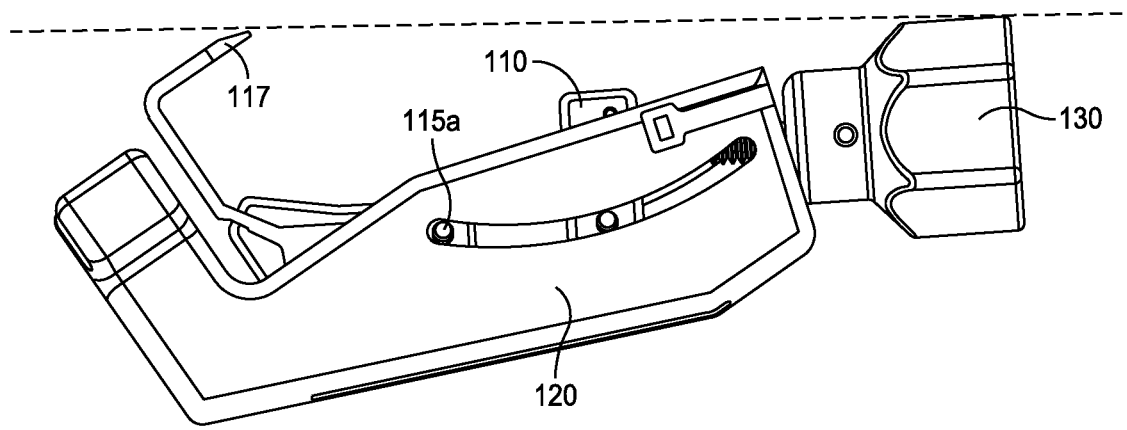
FIG. 12 is a side plan view of an alignment of the outer portion and the inner portion.

The tip 117 of the inner portion 110 of the assembly 100 is configured to be inserted into an intramedullary (IM) canal of the first bone portion B1 to guide and anchor the assembly 100 to the patient. The inner portion 110 and the outer portion 120 are pivotally engaged to each other and can be reoriented with respect to each other by rotating the actuation mechanism 130. Referring to FIG. 12, a first configuration of assembly 100 is provided with the inner portion 110 arranged so that the guide pin 115a is towards one end of the curved slot 124a in the outer portion 120 and the guide 140 not attached to the outer portion 120, the proximal end of the assembly 100 toward the actuation mechanism 130 can be brought more laterally (i.e. aligned with respect to the dotted line which is intended to represent the medial border of the patient's foot) so that the tip 117 can now be angled more laterally as well and eased into the osteotomy.

After the tip 117 of the anchor guide is placed into the IM canal of the first bone portion B1, the guide 140 and the trajectory cartridge 150 can be attached to the outer portion 120 and positioned against the patient's skin. Once in place, the actuation mechanism 130 can be rotated to change the relative position of the inner portion 110 to the outer portion 120 and draw the guide pins 115a, 115b toward the actuation mechanism 130 causing relative rotation such that the skin-interfacing portion 125 contacts and pushes the second bone portion B2 off-axis relative to the first bone portion B1. Effectively, the tip 117 is an anchor that anchors the assembly 100 in place with respect to the first bone portion B1 and guides orientation as the assembly 100 is adjusted to displace the second bone portion B2 and align the targeting sleeves S1 and S2. This action translates the second bone portion B2 into the final desired position.

The interaction between the guide pins 115a and 115b and the curvature of the curved slots 124a, 124b produce the pivoting motion between the inner portion 110 and the outer portion 120 such that as the actuation mechanism 130 is rotated, the skin-interfacing portion 125 moves with respect to the tip 117. Because of the pivoting motion between the inner portion 110 and the outer portion 120, the movement of the skin-interfacing surface 125 is in an arc which matches the curvature of the curved slots 124a, 124b. In the surgical procedure for correcting hallux valgus deformity, the second bone portion B2 of a first metatarsal bone is preferably translated in the lateral direction. The shape of the skin-interfacing portion 125 keeps the second bone portion B2 centered and can prevent the second bone portion B2 from translating in dorsal-plantar directions. Optionally, additional anchoring/fixating elements can be placed through one (or more) of the holes 127 to also help maintain this centering.

As noted above, the trajectory cartridge 150 can include sleeve holes 156 and indicator holes 158. The sleeves holes 156 can receive sleeves S1, S2 to guide trajectory of fixation wires, tools, pins, screws, or the like through the sleeves S1, S2. The indicator holes 158 can receive a K-wire that can be used as an alignment indicator. For example, FIG. 13 shows that the K-wire K that has been inserted through one of the indicator holes 158 is substantially aligned with the sleeve S1 under the K-wire K. This alignment can be performed visually or using an imager such as an X-ray. As shown, when aligned, the length of the K-wire K effectively visually extends the trajectory of the sleeve S1 through the first bone portion B1 and into the second bone portion B2. Thus, the trajectory of a reaming device or drill used to create a pilot hole for a fixation wire or screw that is inserted through the sleeve S1 will be known before it is inserted.

Patients have variable metatarsal head sizes and variable skin/tissue thickness medial to the metatarsal head. To accommodate the various physical dimensions of the patients, a surgical kit can include a plurality of different trajectory cartridges 150 each with a different configuration of sleeve holes 156 and indicator holes 158. As previously described, one configuration of trajectory cartridge 150 can include sleeve holes 156 and indicator holes 158 that are aligned to be substantially parallel to the longitudinal axis of the protruding portion 154, and other configurations can include sleeve holes 156 and indicator holes 158 that are angularly shifted a small angle away from the longitudinal axis. In any trajectory cartridge configuration, the sleeve holes 156 and indicator holes 158 are meant to be parallel to each other.

Figure 15:
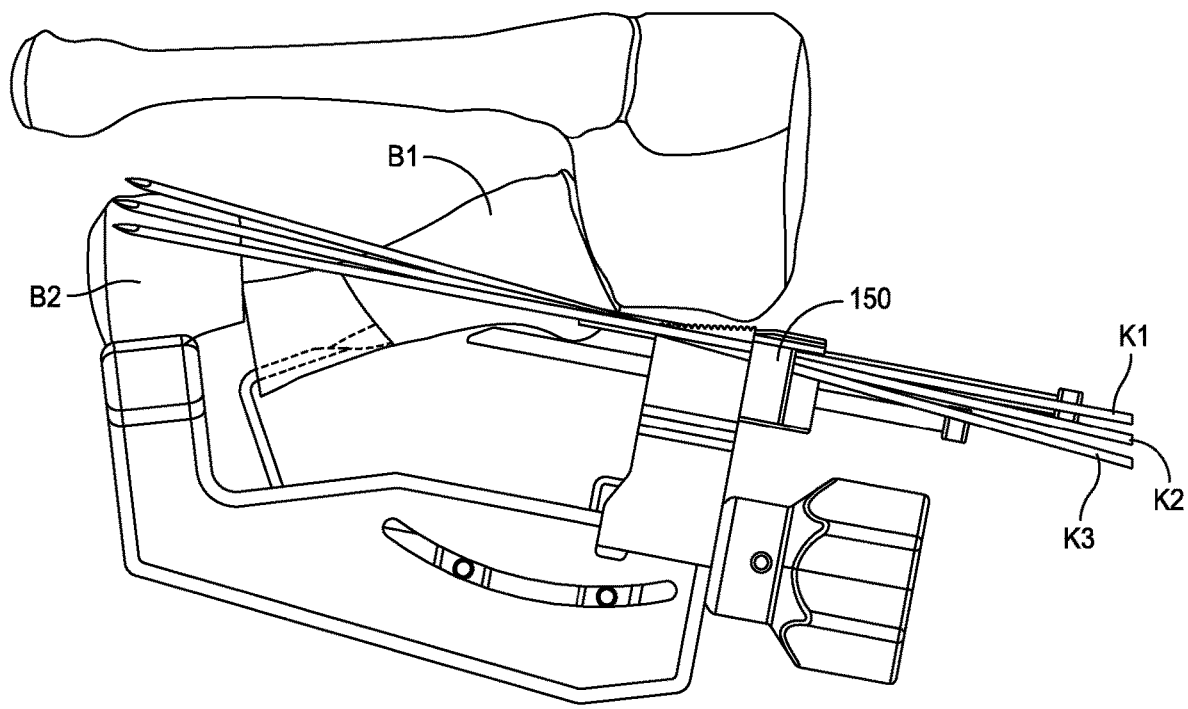
FIG. 15 is a perspective view, similar to that of FIG. 11, illustrating an assembly with different trajectory options.

Optionally, one trajectory cartridge 150 can include multiple configurations of sleeve holes 156 and indicator holes 158. These options are meant to cover a broad range of patients. For example, FIG. 15 shows an assembly 100 with three different trajectory options indicated by alignments of three different K-wires K1, K2, and K3. These options can be provided by one and/or a plurality of trajectory cartridges 150.

Figure 14:
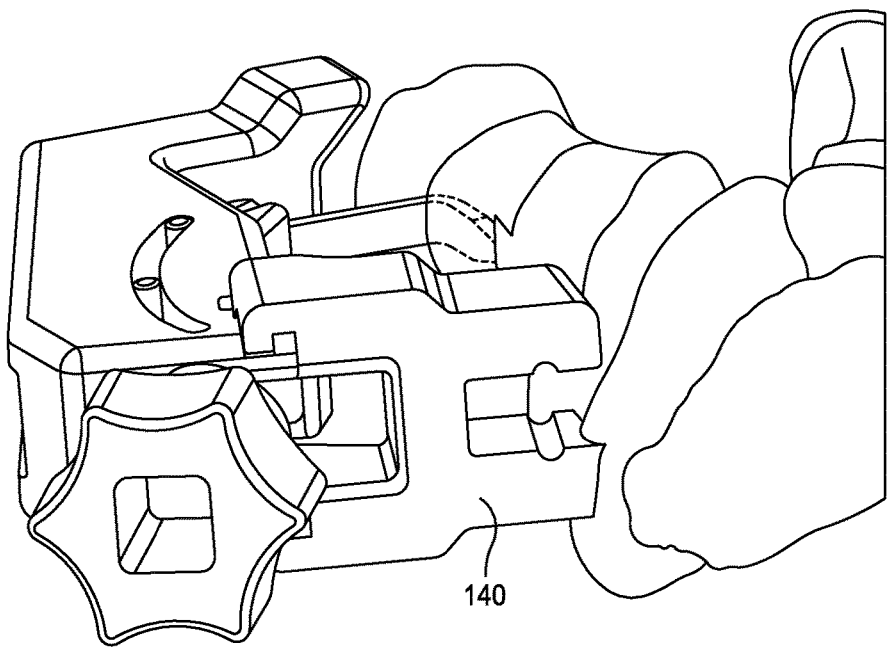
FIG. 14 is an end-on perspective view, similar to that of FIGS. 11 and 13, illustrating an assembly in use with the trajectory cartridge 150 detached from the guide 140.

The trajectory cartridge 150 is easily detachable from the guide 140 so that a trajectory cartridge 150 with proper alignment based on the patient's need and progress of the surgery can be selected. FIG. 14 is a view showing an assembly in use with the trajectory cartridge 150 detached from the guide 140. Removing the trajectory cartridge 150 creates a gap between two skin-contacting walls of the guide 140 where the trajectory cartridge 150 would be, effectively creating a gap between the center of guide 140 and the patient's skin between these contacting walls, providing a space for drilling or screw placement without the need to remove the entire assembly 100 from the patient's foot.

Figure 16:
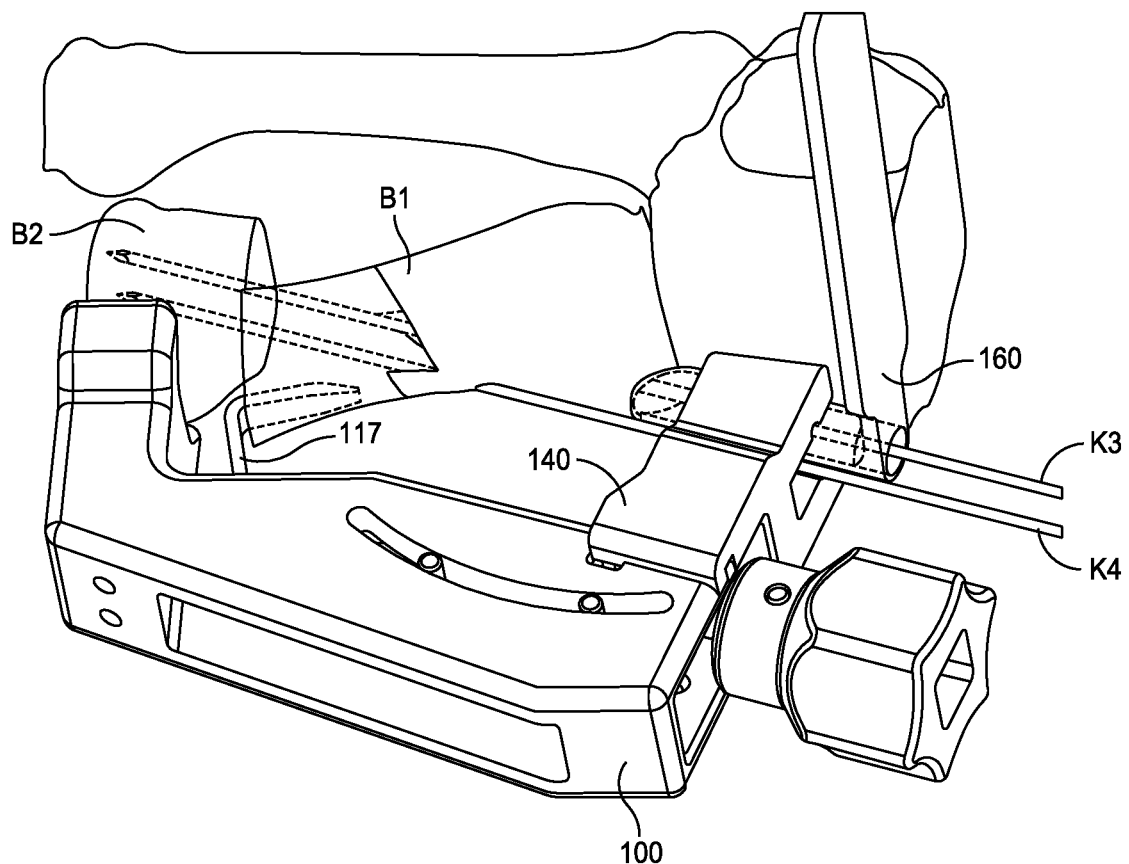
FIG. 16 is a perspective view, similar to that of FIG. 11, illustrating a configuration of the assembly including a tissue protector.
Figure 17:
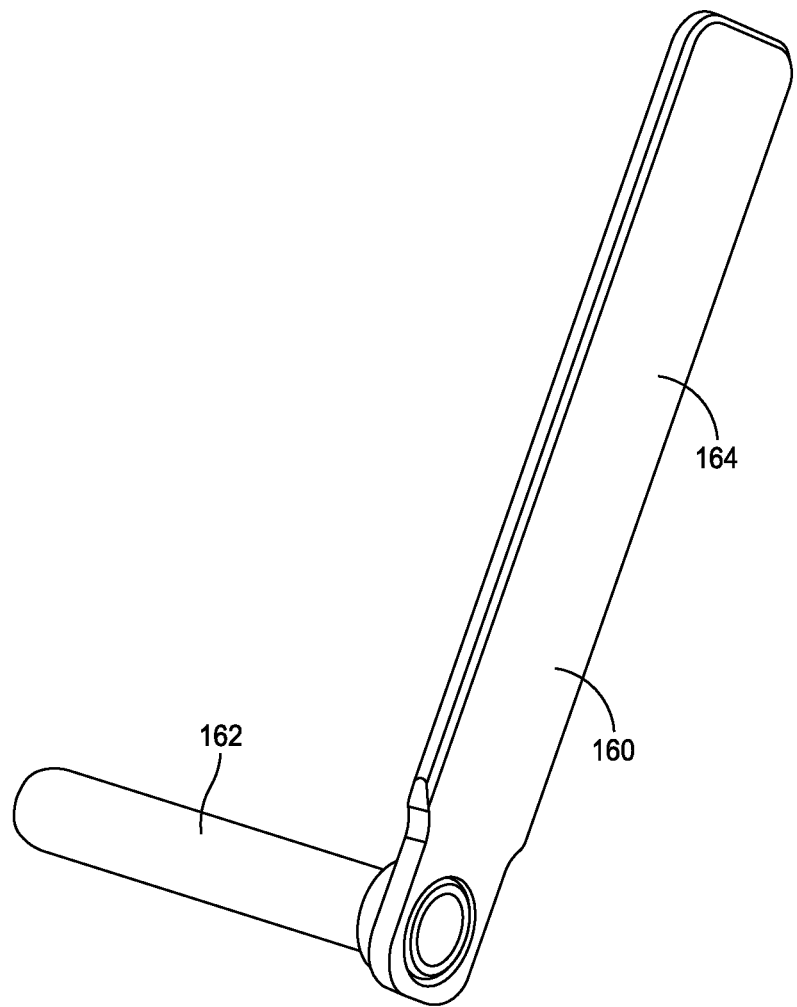
FIG. 17 is a perspective view illustrating the tissue protector according to an embodiment of the invention.

Alternatively, other tools can be attached to the guide 140 in place of a trajectory cartridge 150. For example, FIG. 16 shows a configuration where fixation wires K3 and K4 have been inserted to align and stabilize the first and second bone portions B1 and B2 using a trajectory cartridge. After which, the trajectory cartridge was removed and a tissue protector sleeve 160 was inserted into the gap in the guide 140. As shown in FIG. 17, the tissue protector sleeve 160 can include a hollow cylindrical sleeve 162 and a handle 164. The tissue protector sleeve 160 can be inserted down the fixation wire K3 and pushed up against the patient's skin. In this position, the surgeon can align and drive a cannulated screw down the fixation wire K3, through the tissue protector sleeve 160, through the first bone portion B1, and into the second bone portion B2 while not exposing skin tissue outside of the tissue protector sleeve 160 to the effects of the rotating screw threads that can damage the patient's skin adjacent to the insertion site.

Figure 18:
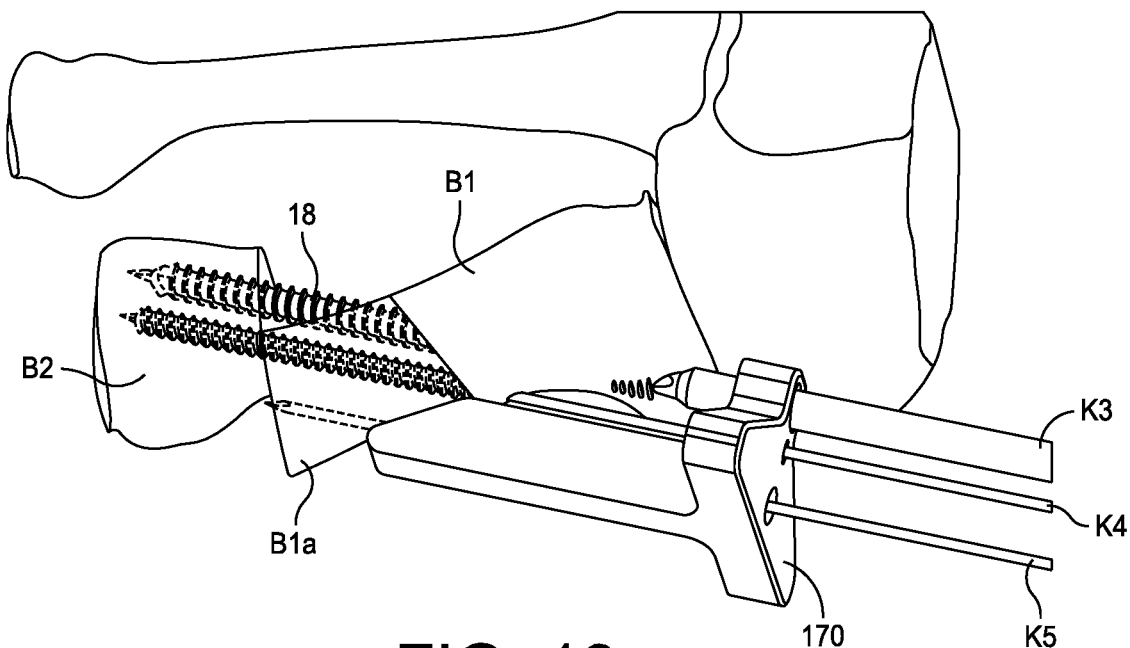
FIG. 18 is a perspective view, similar to that of FIG. 11, illustrating the use of a corner removal tool 170 that can be included in the surgical kit.

FIG. 18 is a view showing the use of a corner removal tool 170 that can be included in the surgical kit. The corner removal tool 170 can be used after screw placement to provide an additional trajectory for a guide wire K5. FIG. 18 shows two cannulated screws, including screw 18, that have been driven down respective fixation wires K3 and K4, through the first bone portion B1, and into the second bone portion B2.

Figure 19:
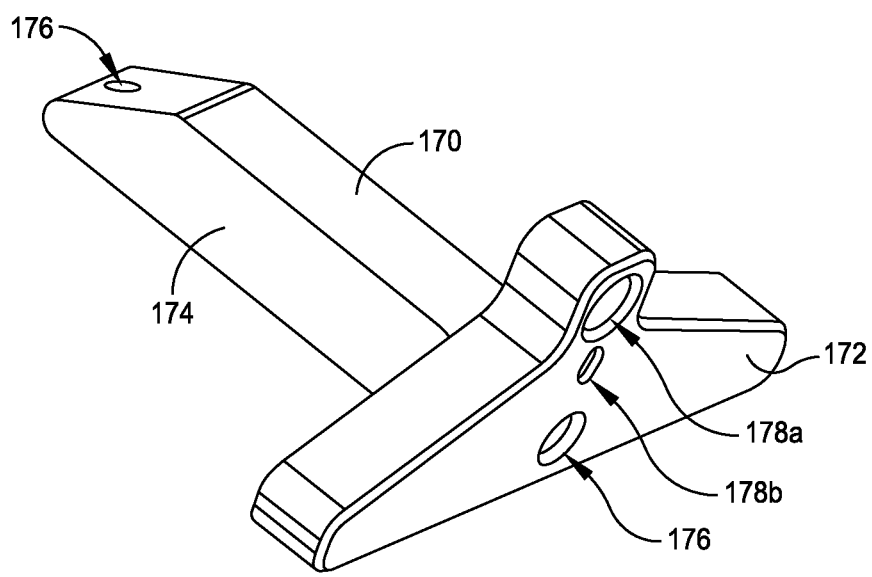
FIG. 19 is a perspective view of a corner removal tool according to an embodiment of the invention.

Referring to FIG. 19, the corner removal tool 170 can be substantially T-shaped with a handle 172 and a shaft 174 extending away from and perpendicular to the handle 172. FIG. 19 also shows that the corner removal tool 170 can include a plurality of holes. As shown in FIG. 18, the alignment holes 178a and 178b can be located and configured such that the corner removal tool 170 can be aligned with and inserted over the fixation wires K3 and K4. FIG. 19 shows that the alignment holes 178a and 178b can be sized to fit fixation wires, sleeves, screws, or tools such as a screwdriver.

Once the guide wire K5 is in place, as shown in FIG. 18, and/or a pilot hole is drilled, the resulting hole can be used to guide the initial placement of a burr or other cutting tool to remove the sharp corner B1a of the first bone portion B1 until the corner B1a is reasonably flush with the new medial border of the corrected foot.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the devices, kits, systems, and methods.

It should be understood that the foregoing description is only illustrative of the invention. Various alternatives and modifications can be devised by those skilled in the art without departing from the invention. Accordingly, the invention is intended to embrace all such alternatives, modifications, and variances that fall within the scope of the appended claims.

I claim:
1. An assembly comprising:
   a first portion including an anchor attached to a first end of the first portion, the anchor configured to be inserted into an intramedullary canal of a first bone fragment;
   a second portion pivotally attached to a second end of the first portion via a sliding pin within a curved slot, and including a first skin-interfacing portion;
   a second skin-interfacing portion configured to interface with and secure the assembly to skin of a patient's foot; and
   an actuation mechanism attached between the first portion and the second portion that actuates a pivoting of the second portion with respect to the first portion; wherein the actuation mechanism is rotated to pivot the second portion with respect to the first portion and to draw the sliding pin toward the actuation mechanism causing relative rotation such that, while the anchor is located in the intramedullary canal of the first bone fragment, the first skin-interfacing portion is configured to contact and push a second bone fragment, adjacent to the first bone fragment, off-axis relative to the first bone fragment.

2. The assembly of claim 1, further comprising a trajectory cartridge attached to the first portion or the second portion and including a first channel aligned to project a trajectory line to the second bone fragment.

3. The assembly of claim 2, wherein the trajectory cartridge includes a plurality of channels including the first channel that are aligned to each project a trajectory line to the second bone fragment.

4. The assembly of claim 3, wherein a longitudinal axis along a length of the first channel of the plurality of channels is parallel to a longitudinal axis along a length of a second channel of the plurality of channels.

5. The assembly of claim 4, wherein the first channel is configured to receive a targeting sleeve and the second channel is configured to receive a guide wire.

6. The assembly of claim 1, wherein the second skin-interfacing portion includes a guide attached to the second portion.

7. The assembly of claim 1, wherein the first skin-interfacing portion is wedge shaped.

8. A kit comprising:
the assembly of claim 1; and
a trajectory cartridge attachable to the assembly and including a first channel aligned to project a first trajectory line to the second bone fragment.

9. The kit of claim 8, further comprising a guide to attach the assembly and the trajectory cartridge.

10. The kit of claim 8, further comprising a plurality of trajectory cartridges wherein each of the plurality of trajectory cartridges includes a different configuration of a channel aligned to project a trajectory line to the second bone fragment.

11. The kit of any of claim 8, further comprising:
a plurality of targeting sleeves, and
a plurality of fixation wires.

12. The kit of any of claim 8, further comprising a tissue protector sleeve that includes a sleeve configured to receive a screw to be inserted into the first bone fragment and the second bone fragment.

13. The kit of any of claim 8, further comprising a corner removal guide configured to guide removal of a portion of the first bone fragment.

14. The kit of claim 13 wherein the corner removal guide includes a plurality of guide holes, a first of which is configured to receive a screwdriver for a screw to be fixed fixed to the first and the second bone fragments, and a second of which is configured to guide the removal of the portion of the first bone fragment.

* * * * *